(12) United States Patent
Mollicone et al.

(10) Patent No.: US 9,030,294 B2
(45) Date of Patent: May 12, 2015

(54) SYSTEMS AND METHODS FOR COLLECTING BIOMETRICALLY VERIFIED ACTIGRAPHY DATA

(75) Inventors: Daniel Joseph Mollicone, Philadelphia, PA (US); Christopher Grey Mott, Seattle, WA (US); Sean Michael Thomas, Irvine, CA (US)

(73) Assignee: Pulsar Informatics, Inc., Philadelphia, PA (US)

( * ) Notice: Subject to any disclaimer, the term of this patent is extended or adjusted under 35 U.S.C. 154(b) by 904 days.

(21) Appl. No.: 13/237,924

(22) Filed: Sep. 20, 2011

(65) Prior Publication Data
US 2012/0068820 A1 Mar. 22, 2012

Related U.S. Application Data

(60) Provisional application No. 61/384,664, filed on Sep. 20, 2010.

(51) Int. Cl.
*G06F 7/04* (2006.01)
*G06F 21/00* (2013.01)
(Continued)

(52) U.S. Cl.
CPC ............ *G06F 21/00* (2013.01); *G06F 19/3431* (2013.01); *G06F 21/32* (2013.01); *G06F 2221/2139* (2013.01)

(58) Field of Classification Search
CPC ..... G06F 19/3431; G06F 19/36; G06F 21/00; A61B 5/4812; A61B 5/4857; A61B 5/1118; A61B 5/4818; A61B 5/117; G06K 2009/00939; G08B 21/0453
USPC ......................................... 340/575–576, 5.82
See application file for complete search history.

(56) References Cited

U.S. PATENT DOCUMENTS 5,433,223 A 7/1995 Moore-Ede et al.
5,682,882 A 11/1997 Lieberman
(Continued)

FOREIGN PATENT DOCUMENTS

JP WO2005000119 6/2005
JP EP1685798 A1 2/2006

OTHER PUBLICATIONS

Sonia Ancoli-Israel, et al., "The Role of Actigraphy in the Study of Sleep and Circadian Rhythms," 26:3 SLEEP 342-392 (2003).
(Continued)

*Primary Examiner* — Firmin Backer
*Assistant Examiner* — Nay Tun
(74) *Attorney, Agent, or Firm* — Damian M. Biondo, Esq.

(57) ABSTRACT

Systems and methods are provided to collect biometrically-verified actigraphy data, comprising: obtaining and processing a subject's measured biometric input from a biometric sensor to generate a current biometric signature of the subject; verifying the subject's identity by comparing the current biometric signature to one previously obtained from a database and evaluating a proximity metric of the current biometric signature of the subject to the previously obtained biometric signature from the database; if the subject passes identity verification, obtaining actigraphy data from an actigraphy sensor worn by the subject; at one or more times while obtaining the actigraphy data, repeating the steps of obtaining and processing a subject's measured biometric input from a biometric sensor to generate a current biometric signature of the subject, and verifying the identity of the subject to ensure that the identity of the subject passes the identity verification at the one or more times.

16 Claims, 10 Drawing Sheets

(51) Int. Cl.
  *G06F 19/00* (2011.01)
  *G06F 21/32* (2013.01)

(56) References Cited

U.S. PATENT DOCUMENTS

| | | | |
|---|---|---|---|
| 5,719,950 A * | 2/1998 | Osten et al. | 382/115 |
| 6,159,130 A | 12/2000 | Torvinen | |
| 6,241,686 B1 | 6/2001 | Balkin et al. | |
| 6,347,040 B1 | 2/2002 | Fries et al. | |
| 6,491,647 B1 | 12/2002 | Bridger et al. | |
| 6,496,724 B1 | 12/2002 | Levendowski et al. | |
| 6,511,424 B1 | 1/2003 | Moore-Ede et al. | |
| 6,513,381 B2 | 2/2003 | Fyfe et al. | |
| 6,516,222 B2 | 2/2003 | Fukuda | |
| 6,527,715 B2 | 3/2003 | Balkin et al. | |
| 6,579,233 B2 | 6/2003 | Hursh | |
| 6,743,167 B2 | 6/2004 | Balkin et al. | |
| 7,189,204 B2 | 3/2007 | Ni et al. | |
| 7,194,113 B2 | 3/2007 | Greschitz et al. | |
| 7,221,928 B2 * | 5/2007 | Laird et al. | 455/404.1 |
| 7,254,255 B2 | 8/2007 | Dennis | |
| 7,254,439 B2 | 8/2007 | Misczynski et al. | |
| 7,424,134 B2 | 9/2008 | Chou | |
| 7,438,225 B2 | 10/2008 | Schneider et al. | |
| 7,733,214 B2 | 6/2010 | Sarig et al. | |
| 7,766,827 B2 | 8/2010 | Balkin et al. | |
| 7,824,888 B2 | 11/2010 | Kondo | |
| 7,898,426 B2 | 3/2011 | Rai et al. | |
| 7,928,830 B2 | 4/2011 | Tsubata et al. | |
| 8,679,012 B1 * | 3/2014 | Kayyali | 600/301 |
| 8,702,607 B2 * | 4/2014 | LeBoeuf et al. | 600/301 |
| 2005/0075116 A1 * | 4/2005 | Laird et al. | 455/456.3 |
| 2005/0131288 A1 * | 6/2005 | Turner et al. | 600/391 |
| 2007/0078351 A1 | 4/2007 | Fujita et al. | |
| 2007/0296601 A1 * | 12/2007 | Sultan et al. | 340/576 |
| 2008/0146892 A1 * | 6/2008 | LeBoeuf et al. | 600/300 |
| 2009/0058660 A1 * | 3/2009 | Torch | 340/573.1 |
| 2010/0130873 A1 * | 5/2010 | Yuen et al. | 600/484 |
| 2011/0044513 A1 * | 2/2011 | McGonagle et al. | 382/124 |
| 2011/0230790 A1 * | 9/2011 | Kozlov | 600/595 |

OTHER PUBLICATIONS

"Practice Parameters for the Use of Actigraphy in the Clinical Assessment of Sleep Disorders," An American Sleep Disorders Assoc. Report, 18:4 SLEEP 285-287 (1995).

Miki Matsumoto, et al., "Assessment of Sleep: Evaluation of the Actillume(R) Wrist Actigraphy Monitor in the Detection of Sleeping and Waking," 52:2 Psychiatry & Clinical Neuroscience 160-161 (1998).

Timothy H. Monk, Daniel J. Buyssee, and Lynda R. Rose, "Wrist Actigraphic Measures of Sleep in Space," 22:7 SLEEP 948-954 (1999).

Charles P. Pollak, et al., "How Accurately Does Wrist Actigraphy Identify the States of Sleep and Wakefulness?," 24:8 SLEEP 957-965 (2001).

* cited by examiner

|   | Actual | | | | |
|---|---|---|---|---|---|
| Predicted | 1 | 2 | 3 | 4 | 5 |
| 1 | 0.987 | 0.017 | 0.000 | 0.054 | 0.000 |
| 2 | 0.006 | 0.961 | 0.000 | 0.007 | 0.000 |
| 3 | 0.006 | 0.000 | 0.989 | 0.007 | 0.000 |
| 4 | 0.000 | 0.000 | 0.011 | 0.933 | 0.000 |
| 5 | 0.000 | 0.022 | 0.000 | 0.000 | 1.000 |

FIGURE 7

Subject 8671

| Enrollment | Distance |
|---|---|
| 8671 | 10.208 |
| 8678 | 39.849 |
| 8679 | 21.768 |
| 8685 | 17.545 |
| 8688 | 139.059 |

Subject 8678

| Enrollment | Distance |
|---|---|
| 8671 | 73.498 |
| 8678 | 26.003 |
| 8679 | 85.235 |
| 8685 | 76.902 |
| 8688 | 76.274 |

Subject 8679

| Enrollment | Distance |
|---|---|
| 8671 | 12.112 |
| 8678 | 60.446 |
| 8679 | 4.137 |
| 8685 | 15.223 |
| 8688 | 159.652 |

Subject 8685

| Enrollment | Distance |
|---|---|
| 8671 | 19.438 |
| 8678 | 51.9 |
| 8679 | 24.059 |
| 8685 | 7.229 |
| 8688 | 149.48 |

Subject 8688

| Enrollment | Distance |
|---|---|
| 8671 | 134.968 |
| 8678 | 86.394 |
| 8679 | 146.534 |
| 8685 | 139.211 |
| 8688 | 13.903 |

FIGURE 8

SYSTEMS AND METHODS FOR COLLECTING BIOMETRICALLY VERIFIED ACTIGRAPHY DATA

RELATED APPLICATIONS

This application claims the benefit of the priority of U.S. application No. 61/384,664 filed 20 Sep. 2010 and entitled SYSTEMS AND METHODS FOR COLLECTING BIOMETRICALLY VERIFIED ACTIGRAPHY DATA which is hereby incorporated by reference herein.

TECHNICAL FIELD

The presently disclosed invention relates to collecting actigraphy data, biometrically verifying the subject's identity and attempting to ensure that the collected actigraphy data is associated with the correct subject.

BACKGROUND

Actigraphy devices measure gross motor activity of a body by deploying motion sensors that may be worn in a variety of places and that may include a wrist (in a watch-like device), leg, shoulder, chest, or some other part of the body. Actigraphy data may be analyzed to determine rest and activity patterns of a person (in this description, the "subject") wearing, or otherwise being sensed by, the device. For example, actigraphy data can be analyzed to evaluate insomnia, to identify restless legs syndrome, to determine levels of daytime physical activity, to assess treatments for sleep disorders, and for other purposes. The determination of sleep timing obtained from actigraphy data may be useful for additional purposes such as assessing whether a subject is receiving enough sleep and estimating at which times the subject is most likely to be subject to the highest risk for fatigue-related incidents.

In certain industries, or for clinical purposes, there may be a desire to collect actigraphy data for a specific subject. By way of non-limiting example, in the trucking industry, actigraphy data may be used to ensure that truck drivers are receiving an adequate amount of sleep. One potential problem with collecting data without oversight of a laboratory environment is that the people on whom such data is being collected may transfer the device, whether mistakenly or intentionally, to another individual thereby corrupting the process of accurate data collection. For example, if a truck driver anticipates receiving less sleep than is necessary for demonstrating readiness for work, he may ask another person that maintains a normal sleep schedule to wear the data-collection device. If the only data collected is actigraphy data, it may be difficult to determine whether the subject that wore the device during a data-collection period was the intended subject.

There is a general desire to collect sleep history information that is accurate and can be reliably associated with a specific subject in a manner that is more robust that using only self-reported subject identity.

SUMMARY

One aspect of the invention provides a method for collecting biometrically-verified actigraphy data. The systems and methods comprise: obtaining measured biometric input in respect of a subject from a biometric sensor and processing the measured biometric input to generate a current biometric signature of the subject; verifying an identity of the subject by comparing the current biometric signature of the subject to a previously obtained biometric signature from a database of previously obtained biometric signatures and evaluating a proximity metric of the current biometric signature of the subject to the previously obtained biometric signature from the database; if it is concluded that the identity of the subject passes the identity verification, obtaining actigraphy data in respect of the subject from an actigraphy sensor worn by the subject; at one or more times while obtaining the actigraphy data, repeating the steps of obtaining the measured biometric input, processing the measured biometric input to generate the current biometric signature of the subject and verifying the identity of the subject to ensure that the identity of the subject passes the identity verification at the one or more times.

Another aspect of the invention provides a system for collecting biometrically-verified actigraphy data. The system comprises: a biometric sensor that outputs measured biometric input in respect of a subject; an actigraphy sensor wearable by the subject that outputs actigraph data when worn by the subject; a controller connected to receive the measured biometric input and configured to: process the measured biometric input to generate a current biometric signature of the subject; verify an identity of the subject by: comparing the current biometric signature of the subject to a previously obtained biometric signature from a database of previously obtained biometric signatures; and evaluating a proximity metric of the current biometric signature of the subject to the previously obtained biometric signature from the database; if it is concluded that the identity of the subject passes the identity verification, procure actigraphy data in respect of the subject from the actigraphy sensor; and at one or more times while obtaining the actigraphy data, repeat the steps of obtaining the measured biometric input, processing the measured biometric input to generate the current biometric signature of the subject and verifying the identity of the subject to ensure that the identity of the subject passes the identity verification at the one or more times.

Another aspect of the presently disclosed invention provides a method for determining the identity of a subject of a device when biometric signature information is available to the device before the data collection begins. In some configurations, the device may only begin data collection after the identity of a subject of the device has been established. In other configurations, the system may allow data collection from an unidentified subject after a certain number of attempts to identify the subject have failed.

Another aspect of the invention provides a method for collection of biometric and actigraphy data concurrently. When information on the device is uploaded to a local or remote computer, the system may then perform data analysis on the recorded information. The data analysis can include determining the unique number of subjects of the device in a given period, which can be established by analyzing the biometric data. Additionally, the system can match each unique subject with a known subject whose biometric signature has been registered with the system.

Yet another aspect of the invention provides for enrolling a single subject's biometric signature on a device. For each set of data that is collected on the device, a percent likelihood that a set of data was collected from the device's enrolled subject can then be calculated. In some implementations, there may be multiple subjects for a given device, and for each data set a percent likelihood can be calculated for each of the enrolled subjects.

Further aspects and features of specific embodiments will become apparent by reference to the drawings and by study of the following detailed description and accompanying drawings.

BRIEF DESCRIPTION OF THE DRAWINGS

In drawings which depict non-limiting embodiments of the invention:

FIG. 7 is an example of classification of five different individuals using the heartbeat waveform as a biometric; and FIG. 8 is an example of matching scores calculated from matching data from five different enrolled individuals against those individual's enrolled biometric signature data.

DETAILED DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense. While actigraphy data is used throughout as an example of the type of data that may be recorded, note that any sort of physiological data that can be digitized via an appropriate sensor could also be recorded and stored.

Aspects of this invention provide systems and methods for collecting actigraphy data from a subject and biometrically verifying the identity of the subject. Some embodiments attempt to ensure that the collected actigraphy data is associated with the correct subject. In particular embodiments, biometric identification involves obtaining (e.g. by sensing or measuring) one or more biometric inputs (referred to in this description as measured biometric inputs) from a subject and matching the measured biometric inputs to previously obtained biometric data (e.g. biometric signatures). A variety of signal processing algorithms may be used to match the measured physiological inputs to the previously obtained physiological data.

Figure 1:
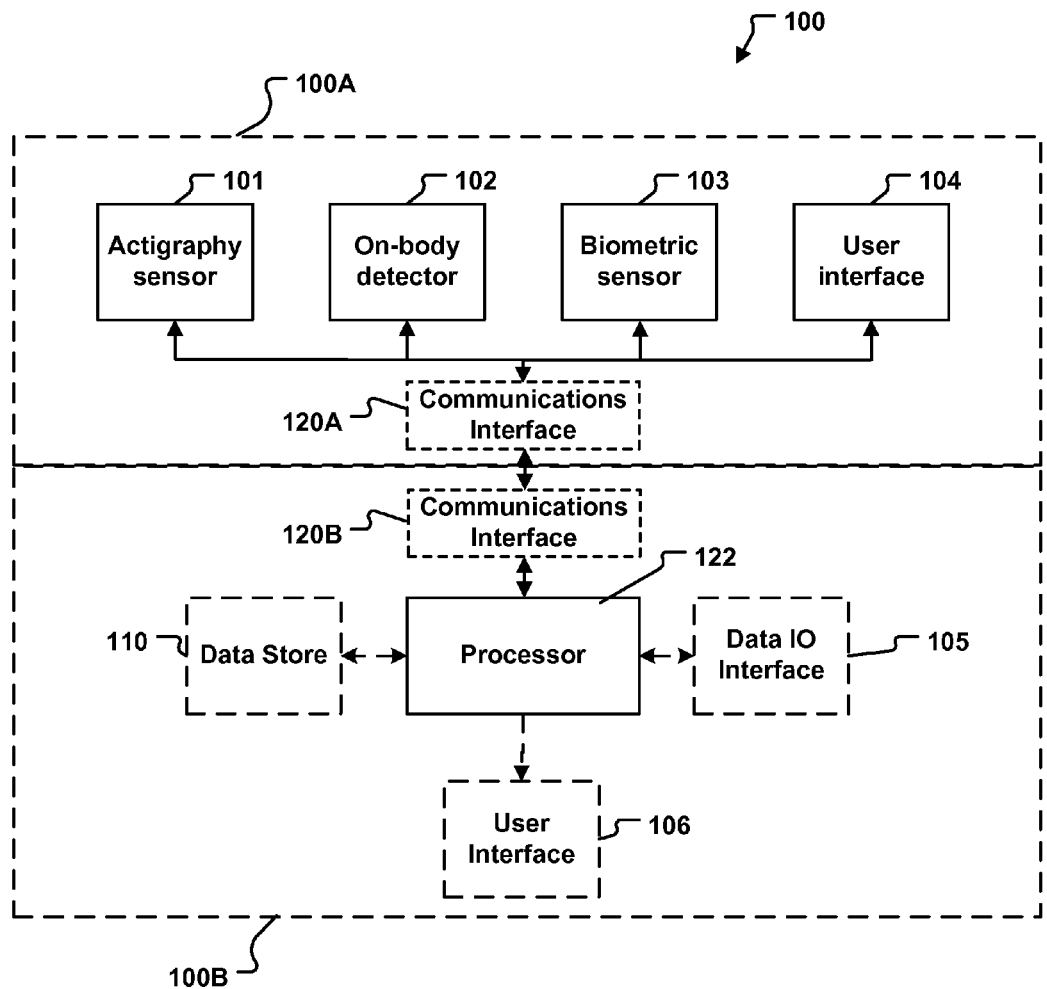
FIG. 1 is a schematic illustration of an actigraphy system with integrated subject identification according to a particular embodiment.

FIG. 1 is a schematic illustration of an actigraphy system 100 with integrated subject identification according to a particular embodiment. In the illustrated embodiment, actigraphy system 100 comprises: a measurement unit 100A to be worn by a subject (or otherwise connected to or associated with a subject in a manner that permits the measurements described below); and a processing unit 100B. In the illustrated embodiment, measurement unit 100A and processing unit 100B communicate with one another via their respective communications interfaces 120A, 120B. Communications interfaces 120A, 120B of measurement unit 100A and processing unit 100B may communicate with one using any suitable technique, including by way of non-limiting example: direct wired communications (e.g. via a USB port and/or the like); direct wireless communications (e.g. via bluetooth and/or the like); wired or wireless network communications using any suitable network communication protocol (e.g. via a local area network, wide area network, cellular communication network and/or the like); and/or the like. It is not necessary that measurement unit 100A and processing unit 100B be separately embodied. In some embodiment, the components of actigraphy system 100 (including both measurement unit 100A and processing unit 100B) may be embodied in a single device. In such embodiments, communications interfaces 120A, 120B may not be required.

In some embodiments, actigraphy system 100 (or at least measurement unit 100A) can be embodied as a wrist-worn device.

In the illustrated embodiment, actigraphy system 100 comprises a processor 122. Processor 122 is schematically illustrated as a single unit. This is not necessary. Processor 122 may be distributed. Processor 122 may generally comprise hardware components and/or software components. Processor 122 may comprise one or more data processors, together with suitable hardware, including, by way of non-limiting example: accessible memory, logic circuitry, drivers, amplifiers, A/D and D/A converters and like. Such data processors may comprise, without limitation, a microprocessor, a computer-on-a-chip, the CPU of a computer or any other suitable microcontroller. Such data processors may additionally or alternatively comprise hardware circuits, which, by way of non-limiting example, may comprise suitably configured field-programmable gate arrays ("FPGAs"), application-specific integrated circuits ("ASICs"); and/or the like. Processor 122 may be programmed with software or may otherwise have access to software (e.g. a program product or the like) which, when executed, may cause processor 122 to implement the methods (and/or portions of the methods) described herein.

Measurement unit 100A of actigraphy system 100 comprises several sensors. Actigraphy sensor 101 captures information related to gross motor activity (referred to herein as actigraphy data). Data collected by actigraphy sensor 101 may be used (e.g. by processor 122) to determine, among other things, whether a subject (not shown) wearing actigraphy sensor 101 was awake or asleep at a given time when the actigraphy data was measured. Actigraphy sensor 101 need not necessarily be worn by a subject. In other embodiments, actigraphy sensor 101 may be otherwise connected to or associated with a subject in a manner that permits the measurement of actigraphy data. For brevity and without loss of generality, this description will assume (unless noted otherwise) that actigraphy sensor 101 is worn by a subject for whom actigraphy data is measured. Suitable actigraphy sensors 101 are known in the art and include 3-axis accelerometers packaged in miniature chips that may be included as part of an electrical circuit. Non-limiting examples of actigraphs and actigraphy sensors may be found within the teachings of: U.S. Pat. No. 6,241,686, entitled "System and Method for Predicting Human Cognitive Performance Using Data from an Actigraph," issued to Balkin et al. on Jun. 5, 2001; U.S. Pat. No. 6,527,715, entitled "System and Method for Predicting Human Cognitive Performance Using Data from an Actigraph," issued to Balkin et al. on Mar. 4, 2003; U.S. Pat. No. 6,743,167, entitled "Method and System for Predicting Human Cognitive Performance Using Data from an Actigraph," issued to Balkin et al. on Jun. 1, 2004; and U.S. Pat. No. 7,766,827, entitled "Method and System for Predicting Human Cognitive Performance," issued to Balkin et al. on Aug. 3, 2010. These references are hereby incorporated herein by reference.

On-body sensor 102 detects whether measurement unit 100A (or more particularly actigraphy sensor 101) is being worn by a subject. By way of non-limiting example, on-body sensor 102 may comprise a proximity sensor of any suitable type—e.g. a capacitive proximity sensor; an acoustic proximity sensor; an electromagnetic proximity sensor and/or the like. Other non-limiting examples of suitable on-body sensors 102, include: sensors that detect the signals indicative that the subject has changed wearing state—e.g. a buckle open/closed sensor on the strap of a wrist-worn device and/or the like.

Measurement unit 100A also comprises one or more biometric sensors 103 for obtaining (e.g. sensing or measuring) corresponding measured biometric inputs. Typically, such measured biometric inputs comprise measured physiological data about the subject wearing measurement unit 100A. Biometric sensor 103 may comprise any suitable biometric sensor(s) of which there are many types known in the art. Non-limiting examples biometric sensors 103 include: electrocardiogram (ECG) sensors, fingerprint readers, iris or retina scanners, accelerometer sensors for gait analysis and/or the like. In one example embodiment, biometric sensor 103 can comprise a set of electrodes used to record an ECG signal wherein one ECG lead can be on the bottom of a wrist-worn actigraphy system 100 (e.g. against a subject's wrist). In some implementations, the outward facing part of actigraphy sensor 100 may contain a second ECG lead and the subject can touch a finger from the hand on which the device is not being worn to this second lead. Alternatively, ECG leads may be external to actigraphy sensor 100 and attached by a removable wire or wireless data transfer.

Non-limiting examples of biometric sensors and methods for their use may be found within the teachings of: U.S. Pat. No. 6,159,130, entitled "Measuring Method and Measuring System," issued to Torvinen on Dec. 12, 2000; U.S. Pat. No. 6,347,040, entitled "Sensor Device for Sensing Biometric Characteristics, in Particular Finger Minutiae," issued to Fires et al. on Feb. 12, 2002; U.S. Pat. No. 6,491,647, entitled "Physiological Sensing Device," issued to Bridger et al. on Dec. 10, 2002; U.S. Pat. No. 6,513,381, entitled "Motion Analysis System," issued to Fyfe et al. on Feb. 4, 2003; U.S. Pat. No. 7,194,113, entitled "Capacitive Biometric Sensor," issued to Greschitz et al. on Mar. 20, 2007; U.S. Pat. No. 7,254,255, entitled "Biometric Sensor Apparatus and Methods," issued to Dennis on Aug. 7, 2007; U.S. Pat. No. 7,424,134, entitled "Card-Type Biometric Identification Device and Method Therefor," issued to Chou on Sep. 9, 2008; U.S. Pat. No. 7,438,225, entitled "Biometric Authentication Device and Method," issued to Schneider et al. on Oct. 21, 2008; U.S. Pat. No. 7,733,214, entitled "System and Methods for the Remote Measurement of a Person's Biometric Data in a Controlled State by Way of Synchronized Music, Video, and Lyrics," issued to Sarig et al. on Jun. 8, 2010; U.S. Pat. No. 7,898,426, entitled "Alertness Estimator," issued to Rai et al. on Mar. 1, 2011; and U.S. Pat. No. 7,928,830, entitled "Biometric Information Dectecting Apparatus," issued to Tsubata et al. on Apr. 19, 2011. These references are hereby incorporated herein by reference.

Measurement unit 100A comprises a user interface 104, which may include, for example, one or more suitable displays and one or more corresponding input devices (e.g. buttons, a touch screen interface and/or the like). A subject may be able to interact with actigraphy system 100 and may possibly control the operation of actigraphy system 100 via user interface 104. In some embodiments, it may be desirable that a subject not be able to have full control of actigraphy system 100—e.g. it may be desirable to maintain some operability of actigraphy system 100 for an administrator or the like.

In some embodiment, measurement unit 100A may comprise other suitable sensors (not shown). In some embodiments, measurement system 100A may comprise its own independent processor, controller and/or logical components (not shown) which may control the operation of measurement unit 100A independently of processing unit 100B and/or processor 122.

Processing unit 100B of actigraphy system 100 comprises a processor 122. Processor 122 may control the operation of measurement unit 100A and may also receive and process data from measurement unit 100A (e.g. via communications interfaces 120A, 120B). Processor 122 may process measure biometric inputs from biometric sensor 103 and may use such measured biometric inputs to verify the identity of a subject wearing measurement unit 100A. Such identity verification may comprise: processing measured biometric inputs from biometric sensor 103 to develop one or more biometric signatures for the current subject wearing measurement unit 100A; and comparing such biometric signatures to previously biometric data (e.g. previously obtained biometric signatures) which may be stored in data store 110. Processor 122 may associate an identity of an identity-verified subject with actigraphy data collected by actigraphy sensor 101 and may store such identity-verified actigraphy data in data store 110. Processor 122 may analyze data acquired by on-body detector 102 to consider whether measurement unit 100A has been removed from the body of an identity-verified subject and, where measurement unit 100A has been so removed, may cause actigraphy system 100 to prompt for updated identity verification information. Processor 122 may also control the operation of user interface 104

In addition to processor 122, processing unit 100B may comprise a data store 110, a data IO interface 105 and a user interface 106. Data store 110 stores data. Data stored in data store 110 may be received from, or accessed via, user interface 106, processor 122 and/or data IO interface 105. Data store 110 may store program code used by processor 122. User interface 106 may comprise one or more displays, other video output devices, audio output devices and/or the like and one or more corresponding input devices (e.g. keyboards, buttons, touchscreens, pointing devices and/or the like). Subjects and/or administrative users may interact with actigraphy system 100 via user interface 106. Processing unit 100B may also comprise a data IO interface (e.g. a USB port or the like) for interacting with other electronic devices and/or systems. Processing unit 100B may comprise other components (not shown) which will be understood to those skilled in the art.

Figure 2:
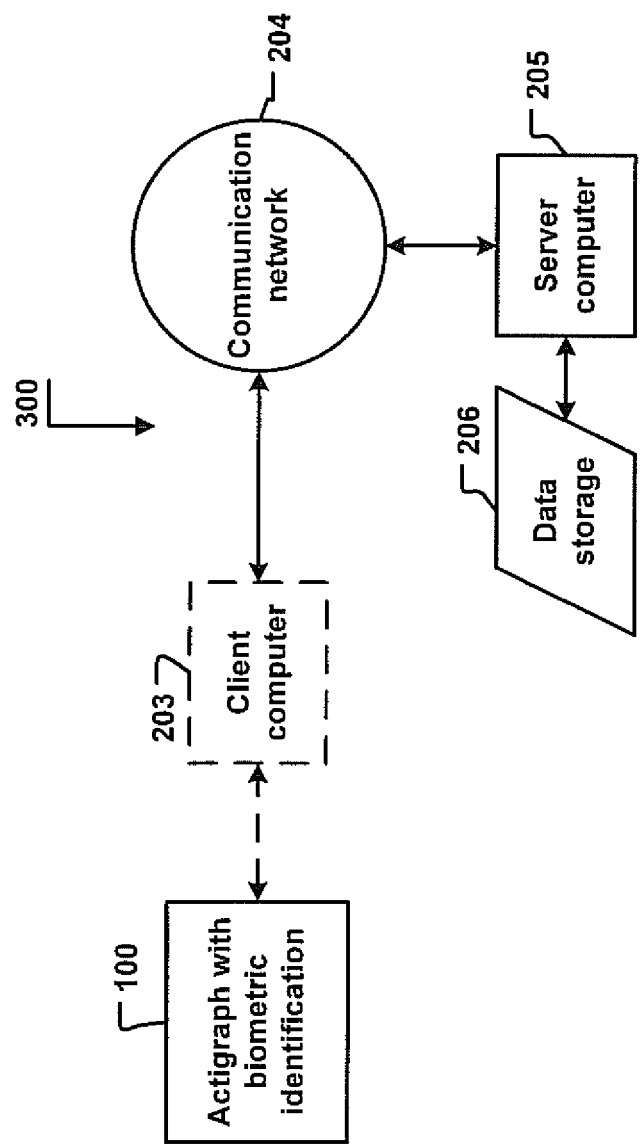
FIG. 2 is a schematic illustration of a system for performing various actigraphy data processing functions on a server computer using a communications network.

FIG. 2 illustrates a system 200 in which the biometrically verified actigraphy device 100 of FIG. 1 may be incorporated into a computer network in accordance with a particular embodiment. Actigraphy device 100 may be in communication with a server computer 205 using a communications network 204. In some implementations, actigraphy device 100 may be capable of utilizing the communications network 204 directly. Such an actigraphy device 100 may be capable of connecting wirelessly to a network using any of IEEE 802.11a/b/g/n, Bluetooth™, cellular networks (4G, CDMA, etc.) or any other means of wireless communication. Actigraphy device 100 may also be capable of connecting directly to a communications network 204 using a wired connection. In another embodiment, actigraphy device 100 may connect to other devices through connections to intermediary devices, such as without limitation an optional client computer 203 using any form of wired or wireless connection type, such as Bluetooth, Zigby, a USB connection, or any other such protocols.

The intermediary devices of system 200, such as optional client computer 203, are then able to retrieve information from the actigraphy device 100 and send data over the communications network 204 to another computer 205. The intermediary devices of system 200 may comprise any device that is capable of retrieving information from actigraphy device 100 and sending the retrieved information to a server computer 205.

Server computer 205 may either have an internal data store 206 or access to an external data storage service. Data store 206 may contain—for either a single subject or all subjects of the server computer 205—a record of collected actigraphy data, biometric signature data, subject credentials, information about a subject's work schedule, or any other data relevant to the system.

Server computer 205 may be capable of performing identity determination or verification, estimating a sleep schedule from actigraphy and other physiological data recorded by actigraphy device 100, performing a fatigue-risk calculation, or any other computation that may be made using available actigraphy, physiological, and biometric data.

There may also be two-way communication between server computer 205 and either a client computer 203 or actigraphy device 100 operating directly as a client of server 205. The server computer 205 may send information to client computer 203 or client actigraph 100 containing whether identity verification was successful, the identity of a subject of the device, a summary of a subject's sleep pattern as determined by the actigraphy data, or any other information that may have been requested by the client device.

It is possible that biometric signature data and subject credentials (subject identifiers and/or passwords) are either stored on a local device or on a remote server. In the case where the information is stored locally, a subject login process and identity verification can either occur on the local device or on the remote device. In the situation where the credentials are stored on a remote server, the local device can request and receive the credentials from the remote server and then perform the verification and login process locally. Alternatively, the local device may send collected information to a remote server where the verification and login process may then be performed.

Figure 3A:
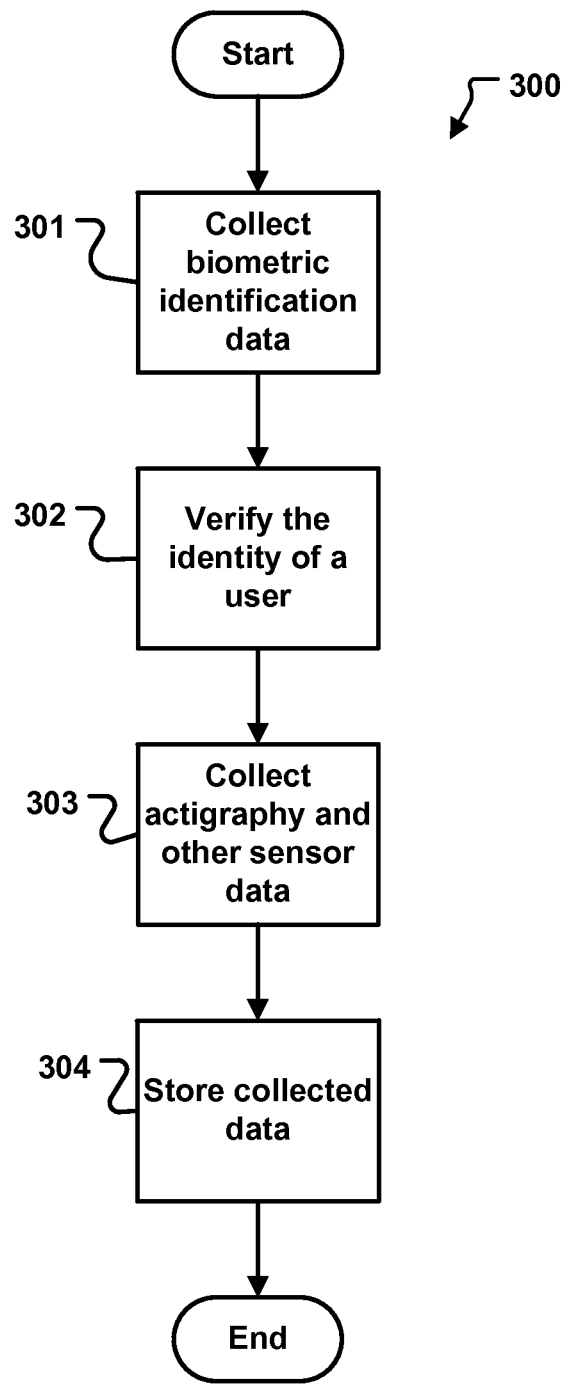
FIG. 3A is a flow chart of a method for collecting actigraphy data and verifying the identity of a subject associated with the collected actigraphy data according to a particular embodiment.

Actigraphy system 100 may be used in the performance of a number of methods according to particular embodiments. FIG. 3A shows a flow chart of a method 300 for collecting actigraphy data and verifying the identity of a subject associated with the collected actigraphy data according to a particular embodiment. Method 300 commences in block 301 which involves collecting measured biometric inputs. In one particular embodiment, measured biometric inputs may be obtained in the form of one or more ECG signal. In other embodiments, block 301 may involve obtaining other forms of measured biometric inputs.

Method 300 then proceeds to block 302 which involves determining whether the block 301 measured biometric inputs can be verified to match the previously recorded biometric data (e.g. of a previously registered subject). Block 302 may involve processing the block 301 measured biometric inputs to generate one or more biometric signatures corresponding to the current subject. There are various techniques known in the art for processing biometric inputs to obtain corresponding biometric signatures which may be used in block 302. Such techniques may depend the nature of the block 301 measured biometric inputs. Block 302 may also involve comparing the block 301 measured biometric inputs (and/or biometric signatures generated therefrom) to previously stored biometric signature data. The block 302 verification may be performed on a local actigraphy system and/or device, or may be performed on a remote server or other device to which measured biometric inputs are transferred.

In some embodiments, a subject may be asked to provide subject credentials (e.g. through one of the user interfaces of actigraphy system 100). Subject credentials entered in this manner may be used to look up a specific subject's previously stored biometric signature. Subject credentials may comprise one or more of a password, subject name, unique security key, and/or other such information. If subject credentials are provided with the block 301 measured biometric inputs, then block 302 may involve checking that the credentials are correct and determining whether the block 301 measured biometric inputs matches the stored biometric signature data associated with the provided credentials.

If no subject identifier or credentials are provided with the block 301 measured biometric inputs, the block 301 measured biometric inputs (and/or signatures generated therefrom) may be compared to previously recorded biometric signatures data previously until a match criterion is met or until the database of previously recorded biometric signature data is exhausted. Suitable match criteria may involve selecting the closest match and then using some suitable metric to determine whether the match between the block 301 measured biometric inputs (and/or signatures generated therefrom) and the previously stored biometric signatures is close enough to verify the identity of the current subject. In some embodiments, a percent likelihood may be determined instead of a binary match or no-match decision.

If the identity of the subject is not verified in block 302, method 300 may stop (not shown) or may revert back to block 301 (not shown) to collect more measured biometric inputs and repeat an attempt to verify the identity of the subject in block 302. In some implementations, if a sufficient number of failed subject identification attempts occur, then method 300 may involve blocking (not shown) further subject identity verification attempts. In one embodiment if the current subject's identity cannot be verified in block 302, the subject may be prevented from recording actigraphy data. Alternatively, method 300 may still proceed to collect actigraphy data in block 303, in which case block 302 may involve informing the subject that their identity could not be verified and/or recording an annotation to the effect that the subject's identity was not verified. In some embodiments, block 302 may log failed attempts to verify a subject's identity in suitable record that may be accessed later.

Unless prevented by a failure to correctly verify the identity of the current subject in block 302, method 300 may then proceed to block 303 which involves collected actigraphy data. In addition to collecting actigraphy data (e.g. from actigraphy sensor 101), block 303 may also involve collecting additional measured biometric inputs (e.g. from biometric sensor 103) and/or data from any other sensors (e.g. on-body detector 102) associated with actigraphy system 100. As data during block 303 is collected, it can be stored 304. In some embodiments, data from on-body detector 102 may be used to detect whether measurement unit 100A was removed from the body of the current subject. Method 300 may involve detecting such sensor removal events and may take one or more suitable actions, such as discontinuing the collection and/or storage of actigraphy data, prompting the subject to put measurement unit back on, returning to block 301 (e.g. to require an additional subject identity verification and/or the like).

Figure 3B:
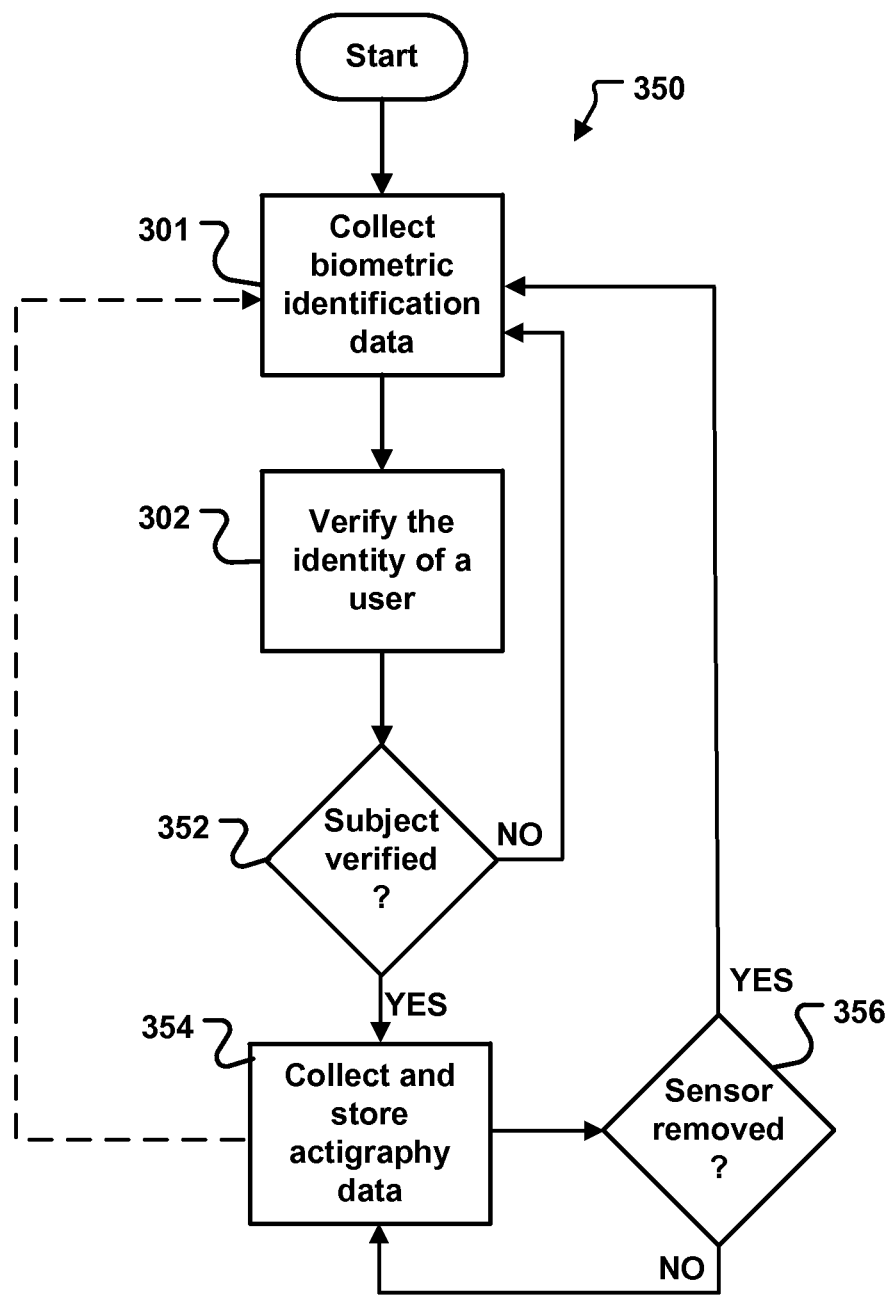
FIG. 3B is a flow chart of a method for collecting actigraphy data from a subject, verifying the identity of the subject and attempting to ensure that the collected actigraphy data is associated with the correct subject according to a particular embodiment.

FIG. 3B is a flow chart of a method 350 for collecting actigraphy data from a subject, verifying the identity of the subject and attempting to ensure that the collected actigraphy data is associated with the correct subject according to a particular embodiment. In some respects, method 350 is similar to method 300 described above. Method 350 commences in block 301 which is substantially similar to block 301 of method 300 described above and which involves collecting measured biometric inputs. Method 350 then proceeds to block 302 which is substantially similar to block 302 of method 300 described above and which involves using the block 301 measured biometric inputs (and/or signatures derived therefrom) to verify the identity of the current user. Method 350 then arrives at block 352 which involves an inquiry into whether the correct current subject has been verified. In some embodiments, block 352 may involve an inquiry into whether any subject is identified (e.g. if the block 301 measured biometric inputs match any previously stored biometric data). In some embodiments, block 352 may involve determining whether the identity of a subject matches the subject's credentials (e.g. login information and/or the like). Such an inquiry may involve comparing the block 301 measured biometric inputs to particular previously stored biometric data identified by the subject's credentials.

If block 352 concludes that the subject's identity has not been properly identified (block 352 NO output) then method 300 returns to block 301 where the subject is required to repeat the identity verification process. While not explicitly shown, method 350 may take similar actions to those described above (e.g. for method 300) in the event that the block 352 inquiry is negative or is negative too many times. If block 352 concludes that the subject's identity has been properly identified (block 352 YES output) then method 300 proceeds to block 354 where actigraphy data is collected and stored. In many respects, block 354 may be similar to a combination of blocks 303 and 304 of method 300 described above.

From time to time during the collection of actigraphy data in block 354, method 350 may optionally return to block 301 (as shown by the dashed line in FIG. 3B) to repeat the identity verification process of blocks 301, 302, 352. This repetition of the identity verification process of blocks 301, 302, 352 may be used to discourage subject from trying to fake their identities, since the same subject will be required to provide the block 301 measured biometric inputs each time that method 350 returns to block 301. Accordingly, the return from block 354 to block 301 from time to time during the collection of actigraphy data may help to ensure that the collected actigraphy data is associated with the correct subject. In particular embodiments, the times and/or intervals at which method 350 returns from block 354 to block 301 may be random (or approximately random). In particular embodiments, the times and/or intervals at which method 350 returns from block 354 to block 301 may be set by an administrative user.

In addition to returning to block 301 from time to time method 350 involves monitoring the status of on-body detector 102 in block 356. So long as measurement unit 100A (or more particularly actigraphy sensor 101) has not been removed by a subject (block 356 NO output), then method 300 may continue to collect and store actigraphy data in block 354. If on-body sensor 102 provides data indicating that measurement unit 100A (or more particularly actigraphy sensor 101) has been removed by a subject (block 356 YES output), then method 300 returns to block 301 which involves re-administering the identity verification process of blocks 301, 302, 352.

Figure 3C:
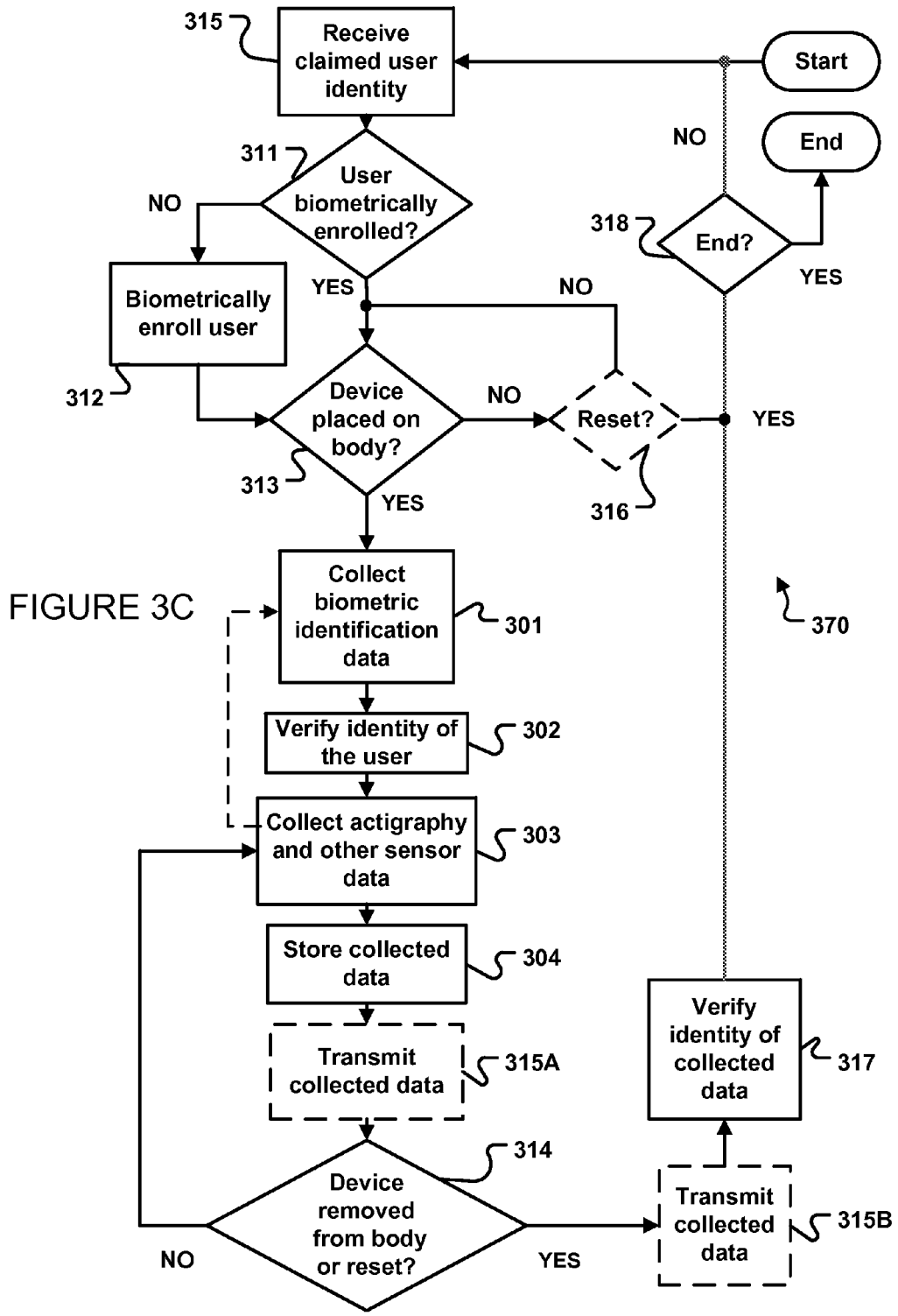
FIG. 3C is a flow chart of a method for collecting actigraphy data from a subject, verifying the identity of the subject and attempting to ensure that the collected actigraphy data is associated with the correct subject according to another particular embodiment.

FIG. 3C is a flow chart of a method 370 for collecting actigraphy data from a subject, verifying the identity of the subject and attempting to ensure that the collected actigraphy data is associated with the correct subject according to another particular embodiment. Method 370 starts with receiving a claimed identity of a subject in block 315. The subject's claimed identity may be provided in the form of log-in information and/or the like. Such log-in information may be selected from a list of subjects or otherwise entered via one of the user interfaces of actigraphy system 100. Block 315 may also involve creating a new subject identity. In some embodiments, a particular actigraphy system 100 may be associated with a particular subject, in which case the block 315 claimed subject identity may be determined a priori. Block 315 may not require a subject to select a claimed identity every time that actigraphy system 100 is used. For example, block 315 may involve using the same identity as that of a previous iteration unless there is some indication otherwise. In certain embodiments, method 370 may permit only allow one subject to be active at a time. In such embodiments, block 315 may involve changing the claimed subject identity.

Method 370 proceeds, in block 311, with a determination as to whether the subject associated with the block 315 claimed identity is biometrically enrolled. Block 311 may involve checking whether a specific subject's biometric signature data and/or credentials have been previously stored. Checking for a subject's biometric signature data as a part of block 311 may be performed by: one or more of checking a local data store (e.g. data store 110 of actigraphy system 100); checking a data store of a remote device via a suitable communications network; and first checking a local data store and then checking a remote data store.

If a particular subject has not been previously biometrically enrolled (block 311 NO output), then the subject can be biometrically enrolled in block 312. The biometric enrollment of a subject in block 312 may happen in a number of ways. By way of example, a subject's biometric signature data may be requested over a suitable communication channel to another device or service. Non-limiting examples of communicating to another device include using a wired connection to a computer, and over a wireless network to remote server. In a further example, the block 312 process of biometrically enrolling a subject may involve sending a device identifier to a server, then based on the device identifier the server may send a preconfigured set of biometric signatures. Such a technique would allow assignment of specific actigraphy system or device to be limited to use by certain subjects from the server's entire directory of biometric signature data. In yet another embodiment, the server may send all available biometric signature data to the actigraphy system or device. In yet another embodiment, the actigraphy system or device may specify to the server which biometric signature data sets and credentials should be retrieved. Another method for biometrically enrolling a subject to a device 312 may involve using biometric sensors (e.g. biometric sensor 103) of the actigraphy system or device to collect measured biometric inputs from the subject and then using those measured biometric inputs to generate a biometric signature which may be stored locally on the actigraphy system or device and/or uploaded to a server for storage. In some implementations, a subject may also enter a subject identifier and password to be stored as credentials alongside the biometric signature data.

After it has been determined that a subject is enrolled (block 311 or 312) but before biometric identification data is collected in block 301, method 300 may involve determining whether the actigraphy system or device has been placed on the subject's body in block 313. Block 313 may make use of data from on-body sensor 102 (FIG. 1). Block 313 may serve to prevent invalid data from being recorded while the actigraphy system or device is not on a subject's body. Any suitable sensor may be used to detect whether the actigraphy system or device is on the user's body. A number of non-limiting examples of such on-body sensors are described above. If it is determined in block 313 that the actigraphy system or device is not on the body of the subject, then method 370 may return to block 313 via optional reset block 316. Optional reset block 316 may involve checking to detect if the actigraphy system or device has been reset. If the actigraphy system or device has been reset, then method 370 may restart at the beginning.

Once it is determined that the actigraphy system or device is on the body of a subject (block 313 YES output) then method 300 may involve performing the biometric identity verification and data collection procedures of blocks 301, 302, 303, 304 which may be substantially similar to the procedures of blocks 301, 302, 303, 304 described above. Data collection (block 303) and data storage (block 304) may be performed iteratively. Additionally in block 314, a determination can be made as to whether the actigraphy system or device has been removed from the body or reset. Block 314 may be similar to block 356 described above. If the actigraphy system or device is still on the body of the subject, then data may continue to be collected and stored in blocks 303, 304. If it is determined in block 314 that the actigraphy system or device has been removed from the subject's body, then data collection and/or recording may be terminated. This functionality may be used to ensure that once the identity of a subject has been verified, the subject does not remove the actigraphy system or device and attach it to someone else while data recording is still occurring. The block 314 inquiry may also prevent data from being recorded after the actigraphy system or device has been removed. Block 324 may also terminate the processes of collecting and/or storing data in blocks 303, 304 may also be stopped if the actigraphy system or device is reset. Here, "reset" may be understood broadly as a block that halts the ongoing collection and/or storage of data in blocks 303, 304, and may include powering off, subject-initiated reset through a user interface, remote reset via a command over a network, and other such procedures.

In some embodiments, while the actigraphy system or device is collecting and/or storing data in blocks 303, 304, such collected and/or stored data may be transmitted to an external system as a part of optional block 315A. In some embodiments, following a reset or removal of the actigraphy system or device from the subject's body (block 314 YES output), data may also be transmitted to an external system as a part of optional block 315B. Data transmission in blocks 315A and/or 315B may be performed over a wired or wireless communications network or any form of communication interface to an external system. Blocks 315A and/or 315B may involve transmitting data to a server computer that receives data from many associated actigraphy systems or devices or transmitting data to a personal computer such as the subject's computer. Data transmitted in blocks 315A and/or 315B may comprise data recorded from the actigraphy sensor, measured biometric inputs, any other physiological sensors, any created subject credentials, and/or the like. The data transmission may occur manually at the direction of the subject, or may occur automatically either at fixed intervals or whenever a communications channel is available.

Like method 350 of FIG. 3B, from time to time during data collection in block 303, method 370 may optionally return to block 301 (as shown by the dashed line in FIG. 3C) to repeat the identity verification process of blocks 301, 302. This repetition of the identity verification process of blocks 301, 302 may be used to discourage subject from trying to fake their identities, since the same subject will be required to provide the block 301 measured biometric inputs each time that method 370 returns to block 301. Accordingly, the return from block 303 to block 301 from time to time during the collection of actigraphy data may help to ensure that the collected actigraphy data is associated with the correct subject. In particular embodiments, the times and/or intervals at which method 370 returns from block 303 to block 301 may be random (or approximately random). In particular embodiments, the times and/or intervals at which method 370 returns from block 30 to block 301 may be set by an administrative user.

In some embodiments of the invention, if a subject has not been previously biometrically enrolled, then the actigraphy system or device may be activated for the subject, collection of actigraphy and biometric data may begin without verification, and then the data collected from this first sample of biometric data may be stored for subsequent verification of the subject. In some embodiments, a subject's biometric signature data may be updated or adapted based on newly collected measured biometric inputs for the subject. In some embodiments, actigraphy data itself may be used as a source of measured biometric inputs or used to augment measured biometric inputs obtained from other sources. Biometric signatures may be generated from actigraphy data based on one more of: activity timing, activity magnitude, interpreted sleep patterns, and/or other such actigraphy-derived metrics.

Figure 4A:
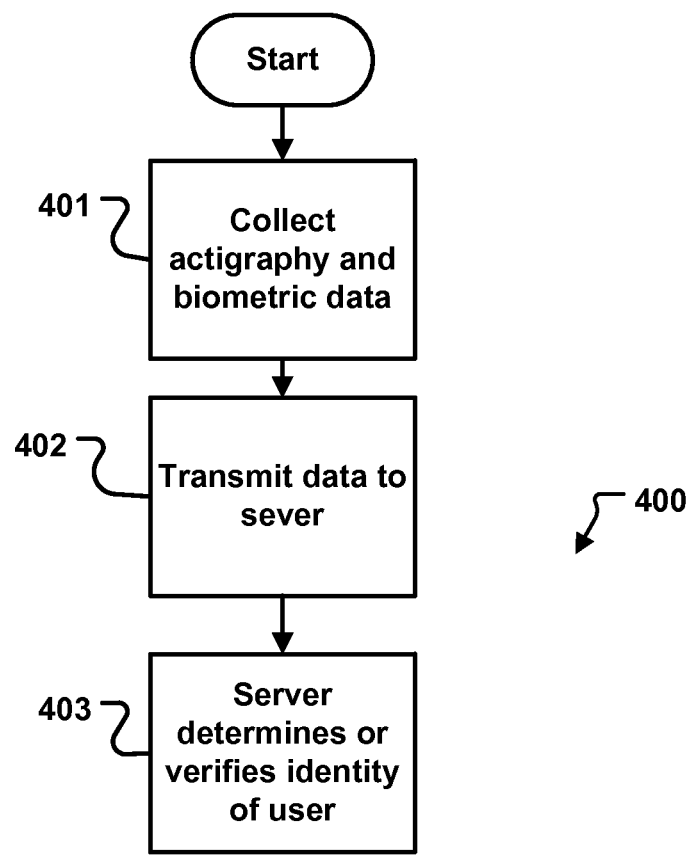
FIG. 4A is a flow chart showing a method for collecting actigraphy and biometric data that is sent to a remote server to determine or verify the identity of the subject and to associate the actigraphy data with the determined subject identity according to a particular embodiment.

FIG. 4A is a flow chart showing a method 400 for collecting actigraphy and biometric data that is sent to a remote server to determine or verify the identity of the subject and to associate the actigraphy data with the determined subject identity according to a particular embodiment. Method 400 starts in block 401 which involves collecting actigraphy and biometric data. Actigraphy data may be collected from an actigraphy sensor (e.g. actigraphy sensor 101), and biometric data may be collected from one or more physiological sensors that measure or sense measured biometric inputs (e.g. biometric sensor 103). The recorded data may also include other physiological data not used for actigraphy or biometric identification. Data from more than one sensor may be recorded at one time.

Method 400 then proceeds to block 402 which involves transmitting the data to a server 402. The block 402 data transmission may occur wirelessly, by a wired connection, or the data may be stored on a removable storage medium that may be removed from the device and placed into another system. In embodiments where the data transmission can occur wirelessly, the data may be transmitted continuously during data collection or whenever a suitable wireless network is available.

After the data has been transmitted to a server in block 402, method 400 proceeds to block 403 to verify or determine the identity of the subject. In particular embodiments, the server may have previously stored biometric signature data and credentials that it uses to determine or verify the identity of the subject. The data transmitted to the server in block 402 may also contain subject credentials or a subject identifier. Subject credentials may comprise one or more of a password, subject name, unique security key, and/or other such information. If credentials are transmitted with the measured biometric inputs, then the server may check that the credentials are correct and determine whether the measured biometric inputs are consistent with the stored biometric signature data associated with the provided credentials. If no subject identifier or credentials are provided with the uploaded data, the server can check the uploaded measured biometric inputs against all of the biometric signature data retained by the server in order to find a closest match. Once a closest match has been found, the server can then determine whether the match between the measured biometric inputs and biometric signature data is close enough to verify the identity of the subject. In some implementations, a likelihood probability or metric may be determined instead of a binary match or no-match decision. The data transmitted to the server in block 402 may also contain an instruction that the uploaded data should be used to enroll a new subject on the server. If this is the case, the uploaded measured biometric inputs can be processed and stored as biometric signature data. If any subject identifier or credentials are provided with the instruction to enroll a new subject, the identifier or credentials can be associated with the new biometric signature data. Additionally, any actigraphy data that was contained in the request to enroll a new subject can also be associated with the newly enrolled subject.

Figure 4B:
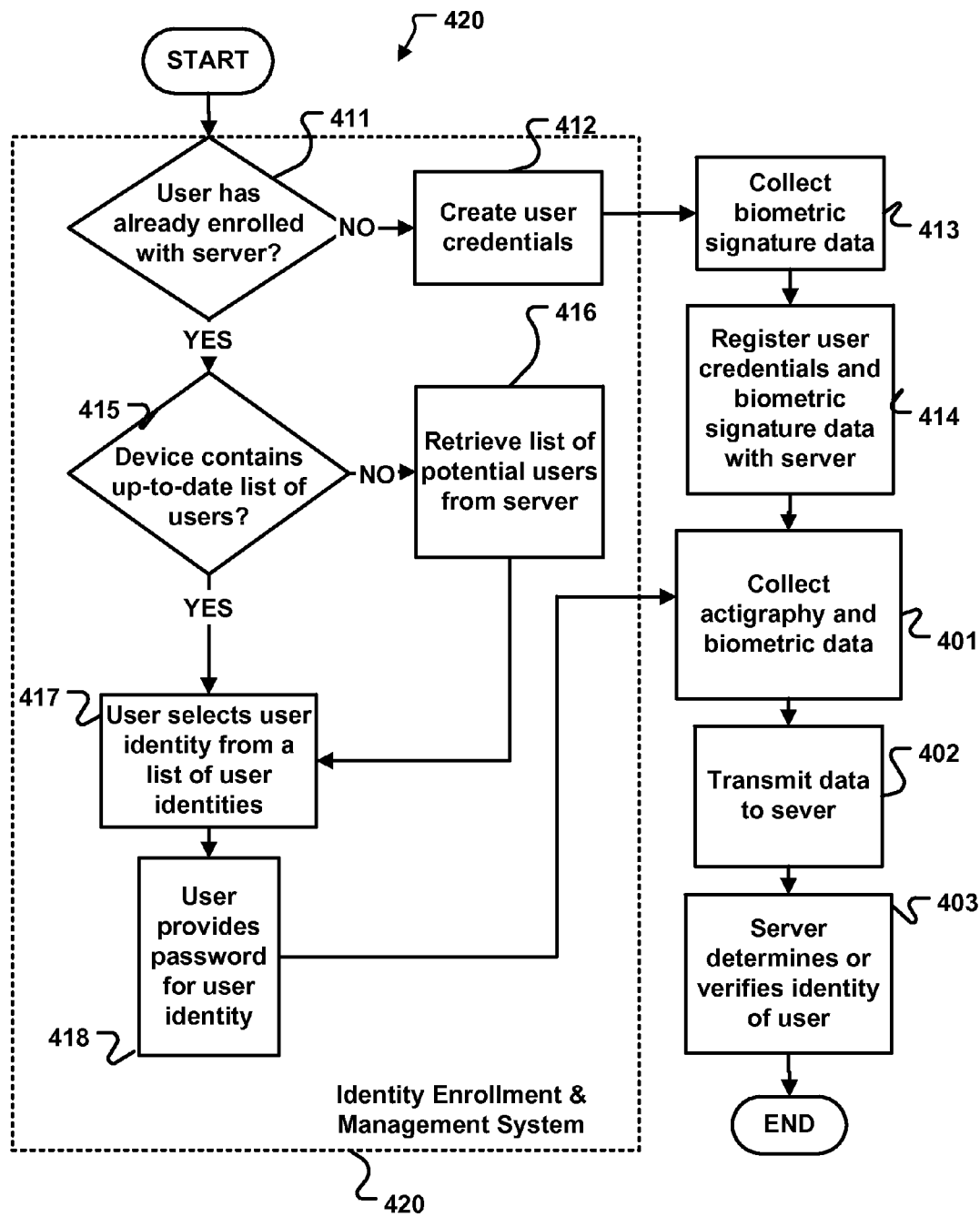
FIG. 4B is a flow chart showing a method for collecting actigraphy and biometric data of one or more subjects and verifying the subjects' identities using a remote server wherein the subject first identifies himself to the system according to a particular embodiment.

FIG. 4B is a flow chart showing a method 420 for collecting actigraphy and biometric data from one or more subjects and verifying the subjects' identities using a remote server wherein the subject first identifies himself to the system according to a particular embodiment. Method 420 involves a number of steps (blocks 401, 402, 403) which may be substantially similar to block 401, 402, 403 of method 400. Before collecting actigraphy and biometric data in block 401, method 420 involves first determining (in block 411) whether a subject has already enrolled with the server. This block 411 determination may be permitted by querying the subject for credential information (in the case that the subject has already enrolled (block 411 YES output)) or asking the subject to confirm that new credentials should be created (block 411 NO output). In some embodiments, a particular actigraphy system or device may support only one enrolled subject. In some implementations, the actigraphy system or device may be preconfigured and provided to a subject with the enrollment already performed. If the subject has not already enrolled with the server (block 411 NO output), then method 400 may proceed to block 412 which involves creating credentials for the subject. In some embodiments, block 412 may involve providing one or both of a subject identifier and password; or, may involve inputting a one-time use registration code. Once the credentials have been created in block 412, measured biometric inputs may be collected in block 413. Collecting measured biometric inputs in block 413 may involve measuring biometric inputs, collecting measured biometric input, ensuring that the collected biometric inputs are valid, and then processing the collected measured biometric inputs into a biometric signature. One way to ensure that collected measured biometric inputs are valid may involve splitting the measured biometric inputs into segments and making sure that the extracted biometric signature is consistent with each segment. Processing the measured biometric inputs into a biometric signature is dependent on the biometric used. An example of how an ECG may be processed into a biometric signature is discussed below. Once the measured biometric inputs have been collected in block 413, the credentials and biometric signature data may be registered with the server 414. These steps of creating a subject identity (block 412), collecting measured biometric inputs (block 413), and registering the subject identity and measured biometric input with the server (block 414) need not all occur on the device that is used to collect actigraphy data.

If the subject has already been enrolled (block 411 YES output), then method 420 may proceed to block 415 which involves determining whether the actigraphy system or device contains an up-to-date list of potential subjects. If the list of potential subjects is not up-to-date (block 415 NO output), a list of potential subjects may be retrieved from the server in block 416 416. Depending on the configuration of the device, the block 416 potential subjects may include all of the subjects whose information is available on a given server, a subset of those subjects, or even a single subject. After the list of potential subjects has been retrieved in block 416 or if it was determined that the device already contains an up-to-date list (block 415 YES output), then the subject may select his identity from a list of subject identities as a part of block 417. If the implementation also requires a password, then the subject may enter his password in block 418. Once the subject has provided his credentials 417, 418, or after a subject has been registered with the server 414 actigraphy and biometric data may be collected by the system in block 401. In some embodiment, block 415, 416, and 417 may be replaced by step which permits the user to enter a user login ID or the like rather than selecting same from a list of subject identifiers.

Figure 5:
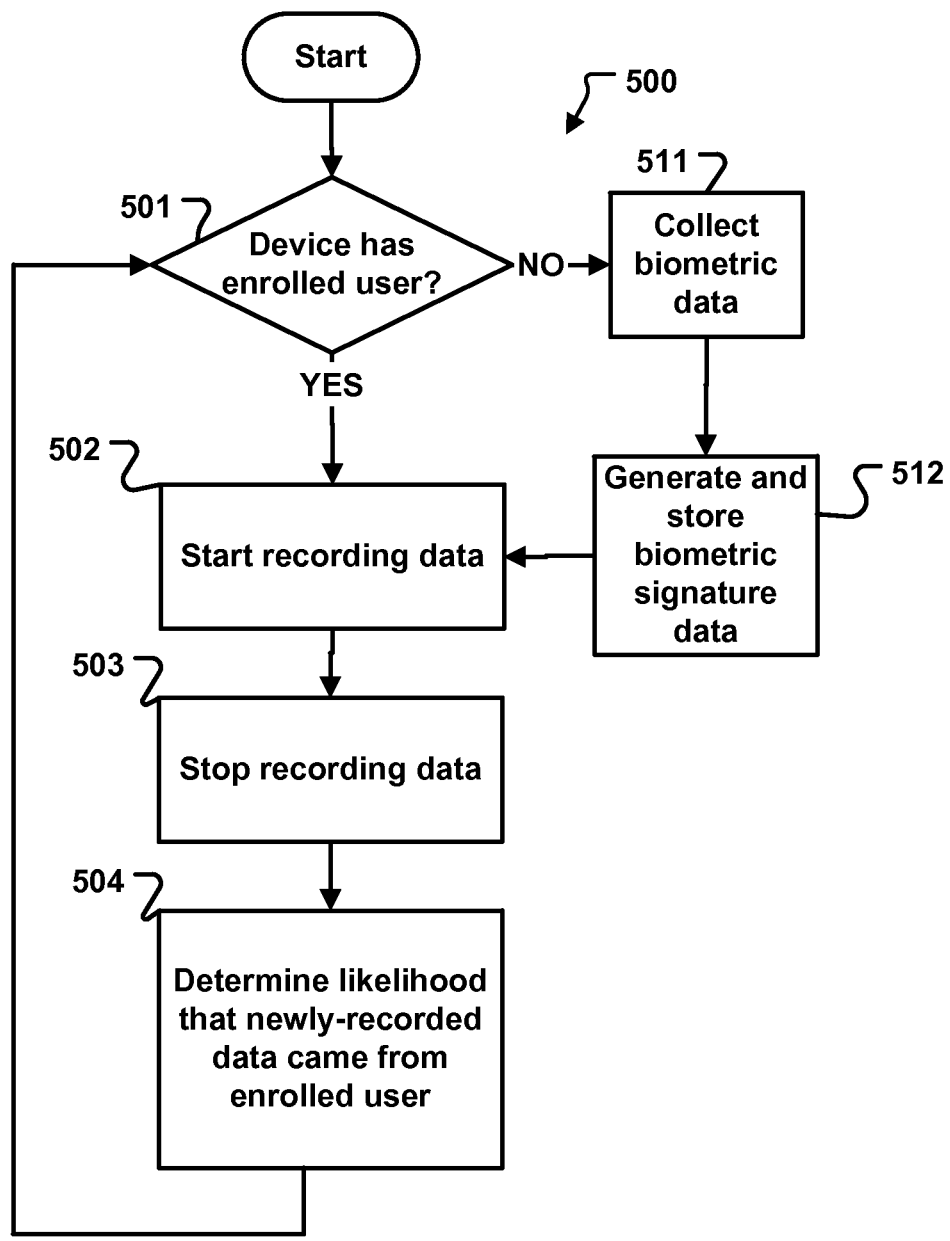
FIG. 5 is a flow chart describing a method for determining the likelihood that a subject wearing the FIG. 1 actigraphy device is the single subject enrolled to that device according to a particular embodiment.

FIG. 5 is a flow chart describing a method 500 for determining the likelihood that a subject wearing actigraphy device 100 is the single subject enrolled to that device according to a particular embodiment. Method 500 starts in block 501 which involves determining whether any subject has been enrolled to actigraphy device 100. If not (block 501 NO output), then method 500 proceeds to block 511 which involves collecting measured biometric inputs. The block 511 collection of measured biometric inputs may be performed by a variety of methods. In one embodiment, the first time that actigraphy device 100 is worn, it may collect measured biometric inputs. Alternatively, the measured biometric inputs may be collected from an external source and then loaded onto actigraphy device 100. There may also be a procedure for removing the enrolled subject from actigraphy device 100. Such a function could either be a readily exposed user interface function or could require special tools or permissions that are only available to a specialized third party (e.g. an administrative user). As discussed above, actigraphy device 100 may support any method of biometric data collection. The selection of enrollment method could be based on a variety of factors including but not limited to, the level of trust an administrator holds in the subject who will be wearing the device, the availability of a third party to verify the identity of the subject, or the level of identity reliability desired. After the measured biometric inputs have been collected or loaded onto actigraphy device 100 during block 511, method 500 may proceed to block 512 which involves generating and storing a biometric signature on the device.

After it has been determined that the device has an enrolled subject (block 501 YES output) or after biometric signature data has been stored on the device in block 512, method 500 proceeds to block 502 which involves recording data. The block 502 recorded data may contain actigraphy data, measured biometric inputs, and any other data gathered by actigraphy device 100. The beginning of the block 502 data recording may be triggered by a user interface element, by on-body detector 102, a timer, or any other event. Sometime later, method 500 proceeds to block 503 where data recording is stopped. As with the start of the block 502 data recording, the trigger discontinuing data recording in block 503 could be a number of different things. Method 500 then proceeds to block 504 which involves determining the likelihood that the newly recorded data came from the enrolled subject. In block 504, newly-recorded measured biometric inputs may be compared to the stored biometric signature data to determine the likelihood that the newly-recorded measured biometric inputs came from the same subject. The procedure for calculating this likelihood would depend on the biometric identification method being used.

In any of the methods described in FIGS. 3A, 3B, 4A, 4B, and 5, there may also be the additional block of a subject entering a subject identifier and a password ("credentials"). In the case where a device is registered for use with a single subject, it may not be necessary to enter a subject identifier. In the case where a device is registered to multiple subjects, the system may only require that a subject enters a subject identifier. Further, in some implementations, it may be the case that a password may serve the dual-purpose of a subject identifier and a password. In some implementations, a subject may be able to choose a specific subject identifier from a list. This additional block could provide an extra level of security to the device. Additionally, it may simplify the biometric identification procedure while making it more secure. For instance, in selecting a subject before biometric verification, the system need only check whether the actual subject of the device is a match to the selected subject. Otherwise, the system would first have to determine which of the enrolled subjects provides the closest match to the actual subject; afterwards, the system could then determine whether the current subject is a close enough match to be verified. This is less secure if there is a large pool of enrolled subject's because with an increasingly large population it becomes more likely that a random subject will be closely matched to a subject that has been previously enrolled in the system.

There many ways in which a subject may be enrolled in a biometric identification system. The following examples of different enrollment schemes are not intended to be limiting in any way. In the situation where an actigraph may only be associated with one valid subject the actigraph may either be in an enrolled or an unenrolled state. If the actigraph is used while it is in an enrolled state, identity verification and any subject login procedure may proceed as normal. If the device is in an unenrolled state, then upon first-use, the device may prompt a subject for his credentials. The credentials may have been preprogrammed into the device, in which case the subject will need to match the preprogrammed information, or this block may serve to register the credentials for the subject. Next, the device may begin recording biometric data. Once the data has finished being recorded, it may be used to generate biometric signature data for the subject, and the device may be placed into an enrolled state. One way that a device may be in an unenrolled state is if the device has never been used before. Also, there may be a method to change the status of a device from an enrolled state to an unenrolled state. This may be simply achieved by placing a reset button on a device or programming a button or touch screen sequence that causes the device to reset. It may also be possible that a device reset is only available with the aid of a third party. The subject of the device could contact the third party, who would then either reset the device or instruct the subject how to reset the device. If the third party resets the device, it may occur remotely over a communications network or it may require the use of specialized equipment that is only provided to trusted third parties.

In a device that allows multiple subjects to be registered on the same device, a similar scheme could be used. Instead of the device either being in an enrolled or unenrolled state, it may be said that a subject is either enrolled or unenrolled. If the subject is not enrolled, then the first time they use the device they may go through the credential creation or verification and biometric signature data generation blocks as disclosed above. A one-time use password may be provided to a subject to begin the enrollment on a device, or a device may contain an option for enrolling new subjects. In some instances, credentials or biometric signature data may be loaded onto a device. The biometric signature data could be recorded using a different physical copy of the same device or different equipment.

In a device that contains a feature for communicating with a server computer, credentials and biometric signature data may be stored remotely. The credentials and biometric signature data may be added to the server computer by a system operator, a third party, or subjects of a device. When someone uses the device, a request may be sent to the server computer for the credentials and biometric signature data. If a connection to the server is not available at the time of use, the subject-provided credentials may be stored on the device and later verified when a connection is available. In another scenario, credentials and biometric signature data that have been retrieved from a server computer may be stored locally on the device. This would lower the number of requests to a server computer for the information, making the device more efficient and increasing its usability in cases where a connection to the server is only available at limited times.

In an instance where biometric data is continuously recorded with the actigraphy data and other physiological data, there are a number of methods by which data may be subdivided for identity verification. For instance, a set of data may be divided by the instances where the device was removed from a body or data recording was halted, and placed into virtual bins. This method of division operates under the assumption that while the device is attached to a body and remains turned on the identity of the subject wearing the device does not change. Another way that the data may be subdivided is by binning the data into segments of a fixed length in time. Each bin may then be used independently to make a determination of the identity of the subject or a percent likelihood that the subject was a specific individual.

From the description above, many combinations and permutations of data collection methods, subject enrollment methods, subject selection methods, device operating modes, server- or client-side data processing methods, and the like should be apparent to one skilled in the art. The exemplary embodiments provided herein are not meant to limit the invention to only the specific disclosed embodiments, but should be understood to include all evident combinations, permutations and modifications of the exemplary embodiments.

Figure 6:
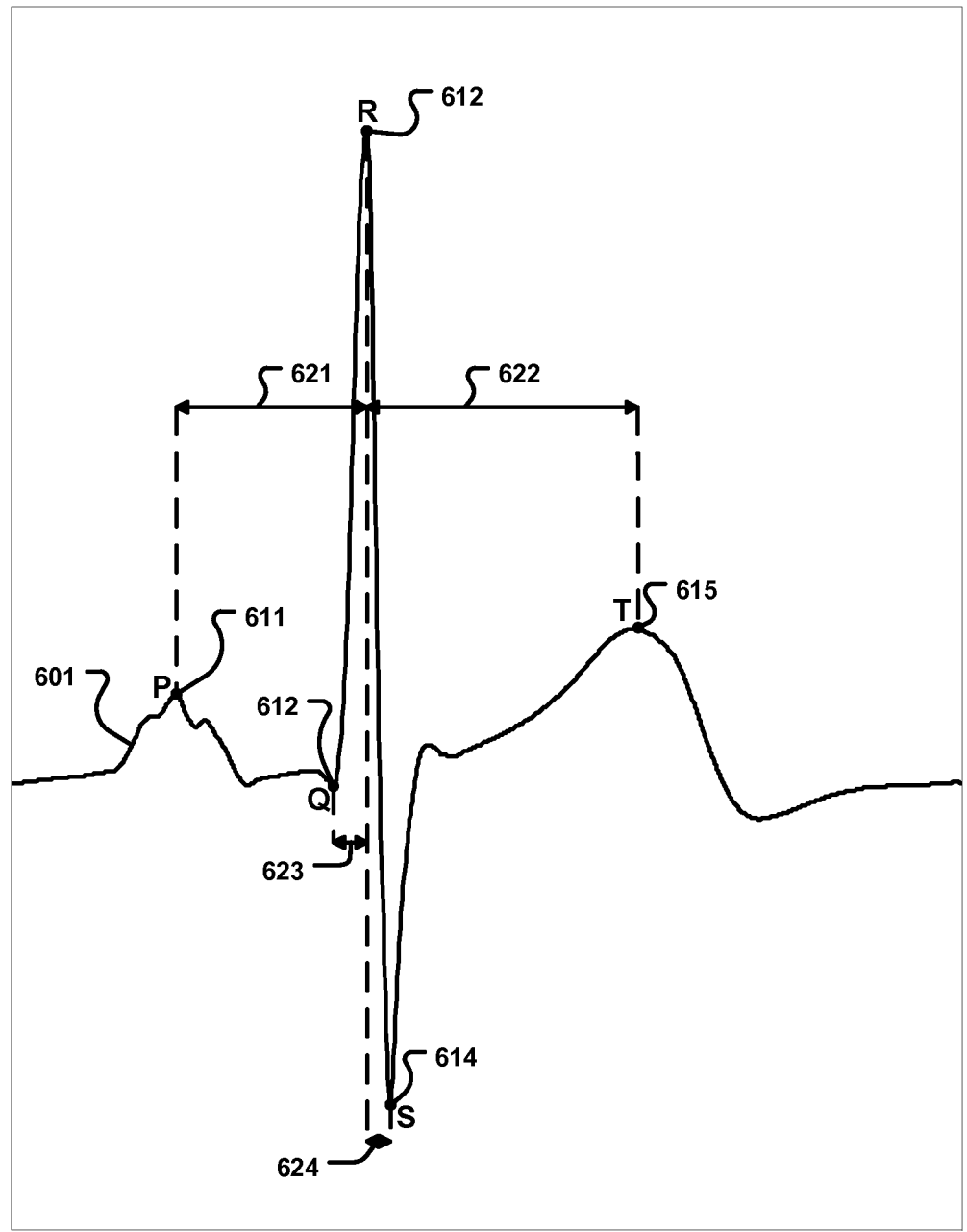
FIG. 6 shows an example of a heartbeat waveform that may be obtained from electrocardiogram (ECG)

One biometric that may be used for identification is that of the heartbeat waveform. The heartbeat waveform may be measured using electrocardiography ("ECG"). FIG. 6 shows an example of a heartbeat waveform that may be obtained from ECG. One way that the heartbeat waveform may be used as a biometric is be correlating averages of the heartbeat waveforms. One drawback to this approach is that the correlations are generally high because of the common features in the heartbeat waveform between individuals. U.S. Pat. No. 7,689,833, "Method and Apparatus for Electro-Biometric Identity Recognition," by Daniel H. Lange, which is hereby incorporated by reference, overcomes this limitation by subtracting the population-average heartbeat from the individual heartbeat.

Another method that may be used involves measuring certain features of the heartbeat waveform. A heartbeat waveform contains a P wave 601, a QRS complex 612, 613, 614, and a T wave 615. Generally, the easiest feature to detect is the R-peak 613. Measurements that may be made from these features include: the P-wave peak to R-peak distance 621, the R peak to T-wave peak distance 622, the Q to R peak distance 623, the R peak to S distance 624, the ratio of the R peak to the P-wave peak, and the ratio of the R peak to the T-wave peak. Additionally, the distance between successive R peaks may be used to determine the heart rate, and the change in heart rate over a given period may be used to determine a measurement of the heart rate variability. Note that usage of "distance" here is synonymous with time interval. Once these metrics have been determined they may be used as inputs to a biometric system to identify an individual or to generate biometric signature data to enroll an individual into the system.

FIG. 7 shows sample results of a classification between five individuals. For each individual, enrollment data and matching data may be obtained. A set of the features listed above could be used as data for the classification system. In the implementation where ECG data is recorded while the device is worn, a large amount of data may be obtained. The overall data set may be divided into bins of a certain time interval, for example fifteen minutes. The mean of the each measurement during each bin may be calculated, and the resulting data may be used as input to a classification system. This serves the function of reducing the amount of data that needs to be processed while also helping to reduce input noise into the system. The combination of all of the individuals' enrollment data may serve as training data to a linear discriminant analysis classification system. Then the matching data may be classified to determine which individual the matching data was recorded from. The diagonal in the matrix presented in FIG. 7 shows the percentage of times that the classification system correctly identified each individual. One feature of this classification system is that the closest match from the set of enrolled subjects will always be selected.

In some cases it may be desirable to determine biometric matching using an independent comparison rather than only selecting the best match among the existing data. This may be desirable in cases where there is a possibility that an individual may use a device and not be previously enrolled. By way of non-limiting example, this may be done using principle component analysis and comparison. First, the principal component vectors of a population data may be determined Before finding the principal components of the population data, the population data may be standardized. One way this may be done is by dividing each metric in the population data by the standard deviation of that metric as calculated from the population data. In a system with multiple enrolled subjects, the population data may be the combination of the data of all the enrolled subjects. In a system with only one enrolled subject at a given time, the population data may be supplied to the system from data collected from a general population study or other such information source. Alternatively, if a set of single-enrollment devices is being used by a business, the population data may be a continually updated data set that is the aggregate of all subjects that have been enrolled on single-use devices for that business. In single-enrollment, the population data may also be supplemented with suitable biometric data from the subject's known associates, family members, and friends. Adding this data to the population data will help the system discriminate situations where the device is used by potential cheaters against those where the device is worn by the intended subject.

Once the principal component vectors have been calculated, a subset of the first N principal component vectors may be retained. This allows the principal components that do not account for much variation between individuals to be discarded. The remaining principal components vectors may be multiplied with the enrollment data sets to map those data sets into the principal component space. Before this multiplication occurs, the enrollment data sets may be standardized using the population data. The average value of each retained principal component may be calculated for the enrollment data sets. This data may be stored as biometric signature data. Then, the geometric distance between the average value of the same procedure applied to a matching data set and a biometric signature may be calculated. If the distance is below a certain threshold, then the subject may be verified as being the same as the subject corresponding to that biometric signature data.

FIG. 8 shows an example of this process. Five individuals were enrolled into a biometric identification system. The entire set of data, comprising enrollment data from each of the five individuals, was used as population data from which the principal components were calculated, and the first five principal components of a total of eight were kept. Each bin of an individual's enrollment data was mapped onto the retained principal components, and the mean of all of the bins from an individual's enrollment data that had been mapped into the principal component space was stored as the biometric signature data for that individual. Then, for each of the five individuals a set of matching data was compared to each of the enrolled data sets. The mean of the geometric distance between each bin of the matching data (mapped into the principal component space) and the biometric signature for each enrolled individual is presented under the "distance" column. For each set of matching data, the lowest resulting geometric distance corresponded to the correct biometric signature derived from the enrollment data.

By rejecting identification attempts with a resulting geometric distance above a certain threshold, subjects that are not actually enrolled in a system may be prevented from being identified as a valid subject. A threshold may be chosen to strike a balance between false positives and false negatives. Some implementations of a biometric identity system may be more adverse to false positives than another.

As an example, one way that the threshold may be set is by mapping the population data into principal component space. As before, only a subset of the total number of principal component vectors may be retained—preferably, the same number that will be used to compare the enrollment data to the matching data. The average of the mapped data for each person in the population data set may then be calculated. If the enrollment data is included in the population data, the population data corresponding to the enrollment data should be excluded from this block. The geometric distance between each of these averages and the average of the mapped enrollment data may then be calculated. The lowest distance may then be used to set a threshold for detection. It indicates the closest non-match as found in the population data. Alternatively, the chosen threshold may be chosen to be somewhat stricter than the lowest distance—for example, ten percent of the lowest distance.

In a single-enrollment case where the output is the percent likelihood that a given subject is the same as an enrolled subject, the distance between the mapped enrolled and matching data sets may still be used. To generate a percentage, the distance score may be mapped onto function that has values between zero and one. An example of such a function is the logistic function. A logistic function could be chosen that is centered on a threshold for identity verification, is one at negative infinity, and is negative one at positive infinity.

For more information on using an ECG signal as a biometric, see the following sources, all of which are incorporated by reference: Lena Biel et al., ECG Analysis: A New Approach in Human Identification, IEEE Transactions on Instrumentation and Measurement, Vol. 50, No. 3, June 2001; U.S. Pat. No. 7,441,123, "Method and Apparatus for Characterizing and Estimating the Parameters of Histological and Physiological Biometric Markers for Authentication", by Grant et al.; and Steven A. Israel et al., ECG to Identify Individuals, Pattern Recognition 38 (2005) 133-142.

Certain implementations of the invention comprise computer processors which execute software instructions which cause the processors to perform a method of the invention. For example, one or more processors in a actigraphy system may implement data processing blocks in the methods described herein by executing software instructions retrieved from a program memory accessible to the processors. The invention may also be provided in the form of a program product. The program product may comprise any medium which carries a set of computer-readable instructions which, when executed by a data processor, cause the data processor to execute a method of the invention. Program products according to the invention may be in any of a wide variety of forms. The program product may comprise, for example, physical media such as magnetic data storage media including floppy diskettes, hard disk drives, optical data storage media including CD ROMs, DVDs, electronic data storage media including ROMs, flash RAM, or the like. The instructions may be present on the program product in encrypted and/or compressed formats.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e. that is functionally equivalent), including components which are not structurally equivalent to the disclosed structure which performs the function in the illustrated exemplary embodiments of the invention.

As will be apparent to those skilled in the art in the light of the foregoing disclosure, many alterations and modifications are possible in the practice of this invention without departing from the spirit or scope thereof. For example:
  actigraphy system 100 may comprise other functionality that may include but is not limited to: a clock, timer, and alarm;
  while actigraphy data is collected in the preferred embodiment of actigraphy system 100 described above, other types of suitable physiological data may be collected in addition to or as an alternative to actigraphy data. Such physiological data measurement systems may collect more than one type of physiological data.

What is claimed is:

1. A method for collecting biometrically-verified actigraphy data, the method comprising:
  obtaining measured biometric input in respect of a subject from a biometric sensor and processing the measured biometric input to generate a current biometric signature of the subject;
  verifying an identity of the subject by comparing the current biometric signature of the subject to a previously obtained biometric signature from a database of previously obtained biometric signatures and evaluating a proximity metric of the current biometric signature of the subject to the previously obtained biometric signature from the database;
  if it is concluded that the identity of the subject passes the identity verification, obtaining actigraphy data in respect of the subject from an actigraphy sensor worn by the subject;
  at one or more times while obtaining the actigraphy data, repeating the steps of obtaining the measured biometric input, processing the measured biometric input to generate the current biometric signature of the subject and verifying the identity of the subject to ensure that the identity of the subject passes the identity verification at the one or more times; and
  providing, while obtaining the actigraphy data, monitoring an on-body sensor associated with the actigraphy sensor to determine if the subject attempts to remove the actigraphy sensor from the subject's body, wherein if monitoring the on-body sensor leads to the conclusion that the subject has attempted to remove the actigraphy sensor from the subject's body, then re-setting a status of the identity verification to an unverified state.

2. The method according to claim 1 comprising randomly generating the one or more times.

3. The method according to claim 1 wherein monitoring the on-body sensor to determine if the subject attempts to remove the actigraphy sensor from the subject's body comprises comparing a signal from the on-body sensor to a threshold.

4. The method according to claim 1 wherein if monitoring the on-body sensor leads to the conclusion that the subject has attempted to remove the actigraphy sensor from the subject's body, then repeating the steps of obtaining the measured biometric input, processing the measured biometric input to generate the current biometric signature of the subject and verifying the identity of the subject to re-evaluate whether the identity of the subject passes the identity verification.

5. The method according to claim 1 wherein obtaining the measured biometric input in respect of the subject from the biometric sensor comprises obtaining a electrocardiogram (ECG) signal from an ECG sensor.

6. The method according to claim 1 comprising obtaining subject credentials from the subject and wherein comparing the current biometric signature of the subject to the previously obtained biometric signature from the database of previously obtained biometric signatures comprises using the subject credentials to identify the previously obtained biometric signature from the database.

7. The method according to claim 1 comprising recording the obtained actigraphy data in a record together with an indicator of the identity of the subject.

8. The method according to claim 1 comprising recording any of the one or more times at which the identity of the subject does not pass the identity verification.

9. A system for collecting biometrically-verified actigraphy data, the system comprising:
- a biometric sensor that outputs measured biometric input in respect of a subject; an actigraphy sensor wearable by the subject that outputs actigraphy data when worn by the subject;
- a controller connected to receive the measured biometric input and configured to:
  - process the measured biometric input to generate a current biometric signature of the subject;
  - verify an identity of the subject by: comparing the current biometric signature of the subject to a previously obtained biometric signature from a database of previously obtained biometric signatures; and evaluating a proximity metric of the current biometric signature of the subject to the previously obtained biometric signature from the database;
  - if it is concluded that the identity of the subject passes the identity verification, procure actigraphy data in respect of the subject from the actigraphy sensor; and
  - at one or more times while obtaining the actigraphy data, repeat the steps of obtaining the measured biometric input, processing the measured biometric input to generate the current biometric signature of the subject and verifying the identity of the subject to ensure that the identity of the subject passes the identity verification at the one or more times; and
- an on-body sensor configured detect a parameter indicative of whether the actigraphy sensor is being worn by the subject, wherein the controller is configured to monitor the on-body sensor to determine if the subject attempts to remove the actigraphy sensor from the subject's body, and wherein the controller is configured to re-set a status of the identity verification to an unverified state if monitoring the on-body sensor leads to the conclusion that the subject has attempted to remove the actigraphy sensor from the subject's body.

10. The system according to claim 9 wherein the controller is configured to randomly generate the one or more times.

11. The system according to claim 9 wherein the controller is configured to monitor the on-body sensor to determine if the subject attempts to remove the actigraphy sensor from the subject's body by comparing the detected parameter to a threshold.

12. The system according to claim 9 wherein the controller is configured, if monitoring the on-body sensor leads to the conclusion that the subject has attempted to remove the actigraphy sensor from the subject's body, to repeat the steps of obtaining the measured biometric input, processing the measured biometric input to generate the current biometric signature of the subject and verifying the identity of the subject to re-evaluate whether the identity of the subject passes the identity verification.

13. The system according to claim 9 wherein the biometric sensor comprises an electrocardiogram (ECG) sensor.

14. The system according to claim 9 wherein the controller is configured to obtain subject credentials from the subject and to compare the current biometric signature of the subject to the previously obtained biometric signature from the database of previously obtained biometric signatures by using the subject credentials to identify the previously obtained biometric signature from the database.

15. The system according to claim 9 wherein the controller is configured to record the obtained actigraphy data in a record together with an indicator of the identity of the subject.

16. The system according to claim 9 wherein the controller is configured to record any of the one or more times at which the identity of the subject does not pass the identity verification.

* * * * *